United States Patent [19]

Stock

[11] Patent Number: 5,037,388

[45] Date of Patent: Aug. 6, 1991

[54] APPARATUS FOR ORAL ADMINISTRATION OF A MEDICAMENT

[76] Inventor: Spencer C. Stock, 19 St. Mary's Road, Kettering, Northants NN15 7BP, England

[21] Appl. No.: 337,847

[22] Filed: Apr. 14, 1989

[30] Foreign Application Priority Data

| | | | |
|---|---|---|---|
| Apr. 15, 1988 | [GB] | United Kingdom | 8808995 |
| Dec. 12, 1988 | [GB] | United Kingdom | 8828952 |

[51] Int. Cl.[5] .................. A61M 31/00

[52] U.S. Cl. .................. 604/57; 604/77; 604/85

[58] Field of Search .................. 604/77, 57, 82, 85, 604/92

[56] References Cited

U.S. PATENT DOCUMENTS

| | | | |
|---|---|---|---|
| 1,208,922 | 12/1916 | Dawkins | 604/77 |
| 2,470,293 | 5/1949 | D'Angelo | 604/92 |
| 4,192,360 | 3/1980 | Rodriquez | 604/77 |

*Primary Examiner*—Stephen C. Pellegrino
*Assistant Examiner*—Michael Rafa
*Attorney, Agent, or Firm*—Scrivener and Clark

[57] ABSTRACT

An apparatus for oral administration of a medicament or the like comprises a pill tray (4) and a liquid reservoir (6). The tray (4) has an upper surface bounded by lips (5) and adapted to carry solid medicament. The reservoir (6) has an opening (7) close to the pill tray (4) and adapted to allow controlled release of said liquid, to wash the pill or medicament down the throat of the patient.

5 Claims, 1 Drawing Sheet

1
2
3
4
5
6
7
8
11
12
13
14
III
III

APPARATUS FOR ORAL ADMINISTRATION OF A MEDICAMENT

The present invention relates to an apparatus for oral administration of a medicament or the like. Particularly, but not exclusively, it relates to an apparatus of the above type for use in administration to a patient who is unable to swallow solid medicaments easily or one who would prefer not to receive any medicament at all.

The term "patient" is used herein in a wide sense to include not only human patients but also animal patients. It is notoriously difficult to administer medicaments, which term again is intended to be used in a wide sense to include medicines, vitamins, preventative medicines, e.g. worm tablets, and even foodstuffs, to animals. Even if one can hold the animal still long enough to insert the tablet in the animal's mouth, there is no guarantee that it will be swallowed. Administering medicines to children may prove equally difficult. Furthermore, it is difficult for some people to swallow solid tablets without also taking a drink.

It is an object of the present invention to provide an apparatus which overcomes some of the above difficulties and allows a medicament to be orally administered more easily.

According to the present invention there is provided an apparatus for oral administration of a medicament or the like comprising tray means having an upper surface adapted to carry solid medicament, and a reservoir for liquid having an opening close to said medicament tray means and adapted to allow controlled release of said liquid.

Preferably the opening is permanently open and disposed in an uppermost surface of the reservoir to allow release of said liquid when the reservoir is inverted.

Alternatively, the opening may be sealed prior to use and unsealed for use. This allows the reservoir to be prefilled, optionally with a measured dose of liquid, which may itself comprise a medicament.

Advantageously a manually closable vent is provided for the reservoir at or near an end thereof remote from the tray means to allow manual control of release of said liquid through said opening.

The reservoir may be elongate and said tray means may be integral therewith and extend from an end thereof.

The apparatus may be dimensioned to be partially insertable into the mouth of a patient and inverted or twisted therein by manual operation of that portion of the reservoir outside the mouth, such inversion causing the solid medicament to fall from the tray means and at least some of the liquid to be released from the reservoir.

Alternatively, the solid medicament, if wetted, may be retained on the tray means by surface effects and be washed therefrom by the liquid released from the reservoir. In this case, it may not be necessary to invert the apparatus.

The means to allow controlled release of said liquid need not be a manually closable vent. Alternatively, a bulb means may be provided, with its interior in communication with the reservoir so that manual pressure applied to the bulb will force the contents of the reservoir through said opening.

In another alternative, the reservoir itself may be constructed, wholly or in part, of a flexible material so that manual pressure to the flexible part of the reservoir will cause egress of the liquid.

The liquid is preferably water, although appropriately flavoured liquids may be used instead. In some cases, the reservoir may be used to administer a medicament in liquid form.

An embodiment of the present invention will now be more particularly described by way of example and with reference to the accompanying drawings, in which.

Figures 1, 2, 3, 4:
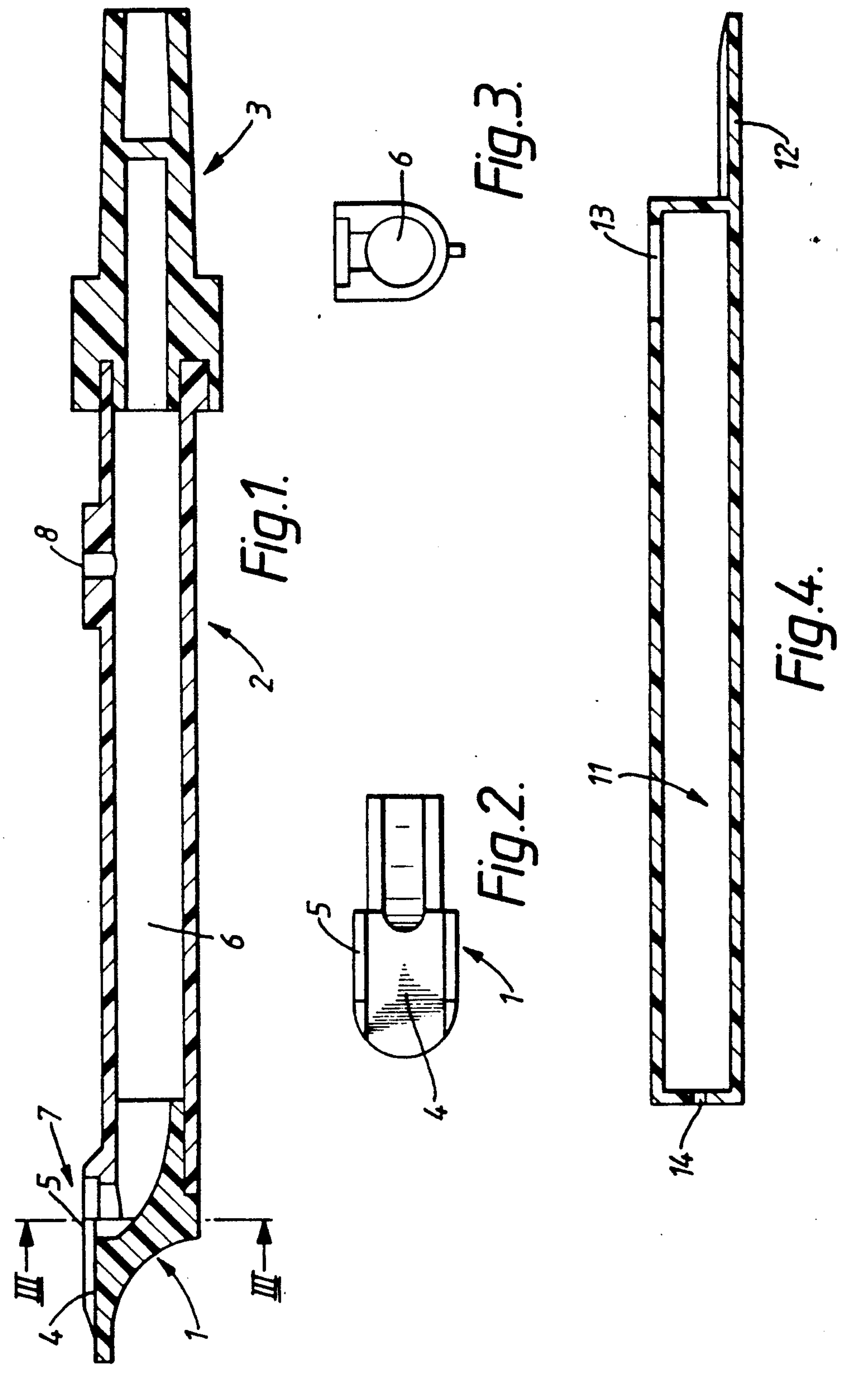
FIG. 1 is a cross-section through one embodiment of the apparatus.
FIG. 2 is a plan view of the medicament tray section of the apparatus.
FIG. 3 is a end elevation of the reservoir section of the apparatus, with the medicament tray section removed, taken along the line III—III of FIG. 1.
FIG. 4 shows a cross-section of another apparatus embodying the invention.

Referring now to FIGS. 1 to 3 of the drawings, the apparatus comprises three joinable sections, a medicament tray section 1, a reservoir section 2 and a handle section 3. The medicament tray section comprises a tray 4 bounded on its sides by lips 5, the lips being adapted to prevent sideways displacement of the solid medicament. Where the medicament tray section 1 meets the reservoir section 2, the interior surface is rounded to provide an end to the reservoir which is adapted to allow the liquid to flow more easily from the reservoir 6 to an opening 7. This opening 7 is formed in part by the medicament tray section 1, and in the remaining part by the reservoir section 2. The external forward face of the medicament tray section may be shaped to contact the tongue of a patient, the better to hold it down during insertion of the apparatus.

The reservoir section 2 is essentially cylindrical, and in the embodiment shown is constructed of a substantially rigid plastics material such as polystyrene. At a point in its upper surface (as seen in FIG. 1) and remote from the medicament tray section 1, is a vent 8. Manual pressure on this vent 8 will prevent escape of the liquid in the reservoir 6 through opening 7. As soon as the manual pressure is released, the liquid can escape.

A handle section 3 is provided to close the other end of the reservoir. It is preferably knurled on at least part of this external surface to permit easy inversion of the apparatus once it is within the patient's mouth.

In another embodiment, not shown, the vent 8 may be covered by a squeezable bulb so that the liquid in the reservoir 6 is forcibly ejected through opening 7. In this case, the vent and bulb may either be in the reservoir portion 2 or in the handle portion 3. In one other embodiment, part or all of the reservoir portion 2 and/or the handle portion 3 may be made of a flexible material which can be squeezed to eject the liquid through opening 7. In this case, the vent 8 may be omitted altogether.

Referring now to FIG. 4 of the drawings, the second embodiment of apparatus comprises a cylindrical reservoir 11 having a part-cylindrical extension 12 at one end. The upper (as seen in FIG. 4) surface of this tray extension 12 is adapted to hold a solid medicament such as a tablet. It need not be part-cylindrical nor need it follow the outline of the reservoir. For example, it may be a flat spade-like projection extending from any convenient point at the end of the reservoir 11. However, it has been found that the part-cylindrical shape better retains the solid medicament during insertion of the apparatus into the patient's mouth.

The reservoir 11 is provided with an opening 13 in its uppermost (as seen in FIG. 4) surface adjacent the extension 12. Thus, liquid is retained within the reservoir 11 while the apparatus is in the disposition shown. A vent 14 is provided at an end of the reservoir 11 remote from the extension 12.

In order to use the apparatus, a pill, tablet or the like is placed on the tray, the reservoir having been filled with water or suitable liquid. The apparatus may be gripped at the end adjacent the vent and inserted into the patient's mouth. Once it is safely inside, the apparatus is inverted causing the medicament to drop from the tray followed closely by the water from the reservoir. With the embodiment shown in FIGS. 1 to 3, the solid medicament may be wetted and will thereby be retained on the tray 4 by surface tension effects. The opening 7 and reservoir 6 are so configured that the liquid exiting through the opening 7 should wash the medicament off the tray 4 when the apparatus is in any orientation. This should cause the medicament to be swallowed more easily, however unwilling or unable the patient is to swallow. The amount of water released can be controlled by placing a finger over the vent to stop any further release.

The embodiment of FIGS. 1 to 3 has been found most advantageous since tests have shown that best results are obtained when the medicament is carried by the liquid. This is because a dry solid medicament, when dropped into the patient's mouth, may immediately stick to the mucous saliva in the patient's mouth. The following liquid may then be swallowed before the bond between the saliva and the medicament is broken. The patient may then be able to reject the medicament. The apparatus of FIGS. 1 to 3 not only carries the medicament more efficaciously towards the patient's gullet — but it has also been found that a slightly wetted medicament is less likely to form a bond with the mucous saliva.

In reluctant patients, it is often a reflex action for the patient's tongue to withdraw itself to the back of the mouth and thereby close the gullet. The shape of the medicament tray portion 1 is adapted to be used to depress slightly the patient's tongue, enough to allow the contents of the reservoir and the medicament to be easily tipped towards an open gullet. This is not always necessary since the presence of cold liquid in the mouth also causes a reflex action where the front part of the tongue (sensitive to cooled liquid) investigates the presence of liquid in the mouth. The tongue cannot investigate the pallet and close the gullet at the same time and therefore the liquid and medicament should have an opportunity to slip into the gullet.

The size of the reservoir portion 2 and the reservoir 6 therein, may be varied depending on the type of patient. For larger animals, and humans, the reservoir may be larger than it would be for small domestic animals such as cats and dogs. The capacity of the reservoir 6 may easily be increased by extending the length of the reservoir section 2. It would even be possible to connect a reserve reservoir (not shown) to the reservoir, for use in emergencies if the dispensed volume of liquid is insufficient to cause the medicament to be swallowed. Such a reserve reservoir could also be used for topping up the reservoir 6 where it was desired to give multiple doses.

The apparatus for use with small animals is preferably moulded from plastics material, such as polystyrene. It is thus light to use, and cheap enough for disposal when it is no longer required. For larger animals, the apparatus may be constructed of other materials, for example metal. The combination of solid medicament immediately followed by water or other liquid should ensure that the medicament is swallowed by the patient. In some cases, the liquid need not be water but may be a flavoured liquid composition to remove any unpleasant after tastes from the medicament.

I claim:

1. An apparatus for oral administration to a patient of a solid medicament comprising tray means having a surface to carry said solid medicament, a reservoir for liquid connected to said tray means, a permanently open opening in an uppermost surface of said reservoir and disposed with respect to said tray means and being of a size that following insertion into a patient's mouth of said solid medicament on said tray means and inversion of said reservoir, liquid exiting from said reservoir through said opening washes said solid medicament towards and down the throat of the patient, and manually operable means to control flow of liquid from said reservoir.

2. An apparatus as claimed in claim 1, wherein said manually operable means comprises a manually closable vent for the reservoir adjacent an end thereof remote from said tray means to allow manual control of release of said liquid through said opening.

3. An apparatus as claimed in claim 1, wherein said tray means and reservoir are dimensioned to be partially insertable into the mouth of a patient and at least partially inverted therein by manual operation of that portion of the reservoir outside the mouth, such inversion causing the solid medicament to fall from the tray means and at least some of the liquid to be released from the reservoir.

4. An apparatus as claimed in claim 1, wherein the solid medicament is wetted to be retained on the tray means by surface effects and be washed therefrom by liquid released from the reservoir.

5. An apparatus as claimed in claim 1, wherein the liquid is water.

* * * * *